(12) United States Patent
Greminger et al.

(10) Patent No.: US 11,304,685 B2
(45) Date of Patent: Apr. 19, 2022

(54) LUNG BIOPSY DEVICES, SYSTEMS AND METHODS FOR LOCATING AND BIOPSYING AN OBJECT

(71) Applicant: Regents of the University of Minnesota, Minneapolis, MN (US)

(72) Inventors: Michael A. Greminger, Duluth, MN (US); Anastasia Zink, Minneapolis, MN (US); Brian Krohn, Saint Paul, MN (US); Amit Goyal, St. Anthony, MN (US); Roy Joseph Cho, Edina, MN (US); H. Erhan Dincer, Saint Paul, MN (US); Felix Zamora, Albuquerque, NM (US); Gills Fai, Duluth, MN (US); Sarah Ostlie, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 654 days.

(21) Appl. No.: 16/026,410

(22) Filed: Jul. 3, 2018

(65) Prior Publication Data
US 2019/0008490 A1   Jan. 10, 2019

Related U.S. Application Data

(60) Provisional application No. 62/528,652, filed on Jul. 5, 2017.

(51) Int. Cl.
*A61B 10/02*   (2006.01)
*A61B 1/00*   (2006.01)
(Continued)

(52) U.S. Cl.
CPC ........ *A61B 10/0233* (2013.01); *A61B 1/0056* (2013.01); *A61B 1/0057* (2013.01);
(Continued)

(58) Field of Classification Search
CPC . A61B 10/0233; A61B 1/0056; A61B 1/0676; A61B 1/00087; A61B 1/0684;
(Continued)

(56) References Cited

U.S. PATENT DOCUMENTS

| 4,432,349 A * | 2/1984 | Oshiro ................. A61B 1/0055 138/120 |
| 8,088,127 B2 * | 1/2012 | Mayse ..................... A61B 8/12 606/41 |

(Continued)

FOREIGN PATENT DOCUMENTS

| WO | WO 2018/175348 | 9/2018 |
| WO | WO 2018/213495 | 11/2018 |

OTHER PUBLICATIONS

International Search Report and Written Opinion, Application No. PCT/US20/17132, dated May 7, 2020, 13 pages.

(Continued)

*Primary Examiner* — Devin B Henson
*Assistant Examiner* — Justin Xu
(74) *Attorney, Agent, or Firm* — Patterson Thuente Pedersen, P.A.

(57) ABSTRACT

According to embodiments, a substantially coaxial arrangement of a camera, a light source, and an ultrasonic sensor can be positioned in an housing of a system that can be deployed from the tool port of a standard bronchoscope. Illumination from the light source facilitates positioning of the system by an operator using information from the camera. The ultrasonic system can determine when an object to be biopsied is adjacent to a biopsy needle.

7 Claims, 13 Drawing Sheets

(51) Int. Cl.
*A61B 1/005* (2006.01)
*A61B 1/06* (2006.01)
*A61B 1/267* (2006.01)
*A61B 8/12* (2006.01)
*A61B 10/04* (2006.01)
*A61B 1/05* (2006.01)

(52) U.S. Cl.
CPC ...... *A61B 1/00087* (2013.01); *A61B 1/00098* (2013.01); *A61B 1/00135* (2013.01); *A61B 1/05* (2013.01); *A61B 1/0676* (2013.01); *A61B 1/0684* (2013.01); *A61B 1/2676* (2013.01); *A61B 8/12* (2013.01); *A61B 1/00009* (2013.01); *A61B 1/00131* (2013.01); *A61B 2010/045* (2013.01)

(58) Field of Classification Search
CPC .............. A61B 1/0057; A61B 1/00135; A61B 1/00098; A61B 1/2676; A61B 1/05; A61B 8/12; A61B 1/00131; A61B 2010/045; A61B 1/00009
See application file for complete search history.

(56) References Cited

U.S. PATENT DOCUMENTS

| | | | |
|---|---|---|---|
| 9,295,454 B2 | 3/2016 | Wang | |
| 10,307,135 B2* | 6/2019 | Naumann | A61B 8/445 |
| 10,595,832 B2* | 3/2020 | Hoffman | A61B 8/0841 |
| 10,695,029 B2* | 6/2020 | Hosogoe | A61B 1/00078 |
| 2006/0178556 A1* | 8/2006 | Hasser | A61B 34/30 |
| | | | 600/102 |
| 2009/0203991 A1* | 8/2009 | Papaioannou | A61B 8/445 |
| | | | 600/421 |
| 2010/0198192 A1* | 8/2010 | Serina | A61B 1/00078 |
| | | | 604/523 |
| 2010/0298640 A1* | 11/2010 | Oneda | A61B 1/00029 |
| | | | 600/109 |
| 2014/0107496 A1* | 4/2014 | Hellstrom | A61B 1/05 |
| | | | 600/478 |
| 2015/0216442 A1 | 8/2015 | Lavy | |
| 2015/0366436 A1* | 12/2015 | Iuel | A61B 1/0051 |
| | | | 600/149 |
| 2018/0049950 A1* | 2/2018 | Besser | A61B 1/0676 |
| 2018/0279868 A1* | 10/2018 | Sczaniecka | A61B 1/0005 |
| 2019/0008490 A1 | 1/2019 | Greminger | |

OTHER PUBLICATIONS

Awaiba, *Image Sensors Product Catalogue*, available at https://www.components-mart.it/datasheets/c2/NANOUSB2.2.pdf, retrieved on May 5, 2021, © 2014, 16 pages.

AMS, *NanEYE: Miniature CMOS Image Sensor*, as available at https://ams.com/naneye, 10 pages, retrieved on May 5, 2021.

Boskovic, et al. "Pneumothorax after Transthoracic Needle Biopsy of Lung Lesions under CT Guidance." *Journal of Thoracic Disease* 6, No. Suppl 1 (Mar. 2014): S99-107.doi:10.3978/j.issn.20721439.2013.12.08.

R. H. Bayford, "Bioimpedance Tomography (electrical Impedance Tomography)," *Annu. Rev. Biomed. Eng.*, vol. 8, No. 1, pp. 63-91, 2006.

Borsic et al., "Electrical impedance tomography reconstruction for three-dimensional imaging of the prostate," *Physiol. Meas.*, vol. 31, No. 8, pp. S1-16, Aug. 2010.

S. Kimura et al. "Application of Electrical Impedance Analysis for Diagnosis of a Pulmonary Mass," CHEST, vol. 105, No. 6, pp. 1679-1682, Jun. 1994.

* cited by examiner

LUNG BIOPSY DEVICES, SYSTEMS AND METHODS FOR LOCATING AND BIOPSYING AN OBJECT

RELATED APPLICATION

The present application claims the benefit of U.S. Provisional Application No. 62/528,652 filed Jul. 5, 2017, which is hereby incorporated herein in its entirety by reference.

TECHNICAL FIELD

Embodiments relate generally to medical examinations and biopsies of the body and more particularly to devices, systems and methods for lung and other biopsies including visual or photographical inspection.

BACKGROUND

Lung cancer is the leading cause of cancer deaths worldwide. There were 180,000 Medicare/Medicaid admissions for bronchial or lung cancer in 2010. In 2013, Centers for Medicare & Medicaid Services paid for 46,000 bronchoscopic lung biopsy procedures. Of these procedures, 3,400 procedures were performed using electromagnetic navigation bronchoscopy (ENB), and 15,300 procedures were performed using endobronchial ultrasound (EBUS).

ENB can be used to track tools within the body using radio waves. Antennas are placed on the patient's body, which receive a signal emitted from the tools inserted into the body. The position of the tool is superimposed onto a CT image of the patient to provide feedback to the physician on the location of the tool. There are at least two ENB systems currently on the market. One such system, the SuperDimension system, is cost-prohibitive for many clinics, at several hundred thousand dollars per unit. A competitor to SuperDimension is the Veran Medical EndoBronchial guidance system, which gained FDA clearance in 2009. The SuperDimension system has a steerable guide catheter with position sensor that is smaller than a bronchoscope. Once the guide catheter is placed, a tool can be deployed through the guide catheter. The Veran Medical system adds some additional features, and supplies a suite of tools that all include the position sensing element at the tip of the tool. They enable the switching from an endobronchial approach to a transcutaneous approach in a single setup. The Veran Medical system likewise can also be cost-prohibited to many clinics or hospitals.

If a transbronchial approach cannot be used to obtain a biopsy, a transthoracic needle can be used to acquire a sample. In 2013, 40,000 transthoracic needle biopsies were paid for by Centers for Medicare & Medicaid Services. The risk of pnuemothorax for transthoracic needle biopsies is between 9 and 54%, however.

EBUS avoids the necessity for use of a transthoracic needle in some instances, where the object to be biopsied is located on a main bronchial tube having a relatively large diameter. EBUS involves using an ultrasonic sensor on a bronchoscope to determine when the bronchoscope is passing by an object having different density or acoustical properties from the rest of the lung. For example, a tumor or nodule can be detected by the difference in acoustical response. The bronchoscope can also include a biopsy needle, such that the detected tumor, nodule, or other object can be biopsied.

EBUS can be implemented on bronchoscopes that are used to biopsy tumors that are in the larger bronchial tubes of the lung. A typical bronchoscope, having a 5.3 mm standard diameter, cannot reach the periphery of the lung, where the bronchial tubes are less than 5.3 mm wide. If the object is adjacent to a large bronchial tube, the EBUS can be routed to it. The edges of the tumor can be seen in the EBUS image generated from ultrasound data.

Existing ENB systems are expensive, and often cost-prohibitive for smaller hospitals or clinics where they would not be used routinely. Furthermore, use of transthoracic needles can result in severe complications such as a collapsed lung. EBUS, while less expensive than ENB, is only suitable when the object to be biopsied is located on a main bronchial path having a large diameter that affords access to the bronchoscope, and much of the lung may be inaccessible to EBUS systems.

SUMMARY

Devices, systems and methods for locating and biopsying an object in a pulmonary system are disclosed. In embodiments, such a system does not require simultaneous electromagnetic navigation bronchoscopy (ENB) guidance or transthoracic puncture, and is capable of reaching objects adjacent to pulmonary passages that are smaller than those reachable by a standard bronchoscope. Systems discussed herein include a tool that is small enough to be deployed by a bronchoscope tool port, and include a camera, light-emitting diode (LED), and ultrasonic sensor.

In one embodiment, a system includes a housing, a camera, a light source, and an ultrasonic system, The housing extends from a proximal end to a distal end. The camera is arranged within the housing at the distal end to obtain optical data relating to the position of the system. The light source is arranged within the housing opposite the camera from the distal end. The light source is then configured to produce illumination passing between the housing and the camera at the distal end. The ultrasonic system is arranged within the housing opposite the light source from the distal end, and is configured to detect acoustical properties in a region opposite the housing from the ultrasonic system. A biopsy needle tube arranged opposite the ultrasonic system from the distal end defines an aperture in the housing, such that a biopsy needle deployed from the biopsy needle tube through the aperture is positioned at the region. The biopsy needle can be bendable, such that the biopsy needle deployed from the biopsy needle tube through the aperture is able to take a biopsy adjacent to a transducer of the ultrasonic system.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Embodiments may be more completely understood in consideration of the following detailed description of various embodiments of the invention in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments discussed herein include a lung biopsy system that can be deployed from a standard tool port of a bronchoscope (i.e., having a diameter of about 2 mm or less) or can be deployed independently. Within this system are arranged, in order from the distal end of the system in one embodiment: a camera; an LED; and an ultrasonic sensor. In other embodiments the ultrasonic sensor may be positioned adjacent to, or may be interchangeable with, the camera and LED. The system can also include a biopsy needle port that facilitates deployment of a needle adjacent to the ultrasonic sensor. Such components can be used to optically guide the system to an object in a pulmonary system to acquire a biopsy sample, even if that object is not located in a large, primary pulmonary passageway that is reachable by the relatively larger bronchoscope.

Figure 1A:
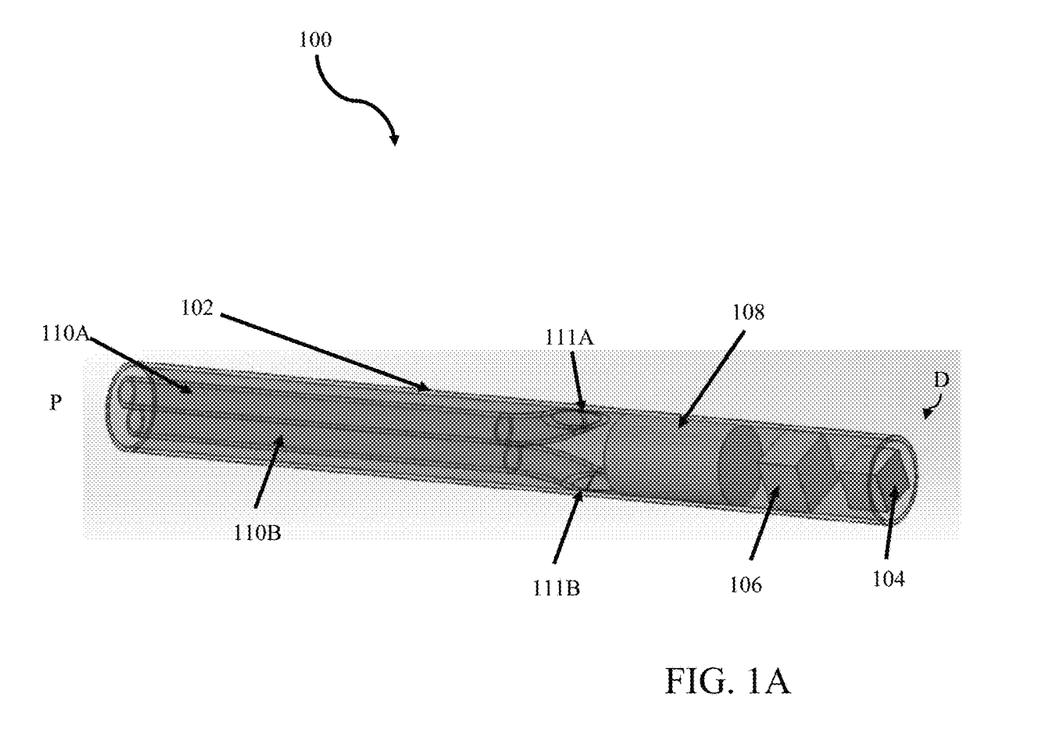
FIGS. 1A and 1B are perspective views of a dual-needle lung biopsy tool according to an embodiment.
Figure 1B:
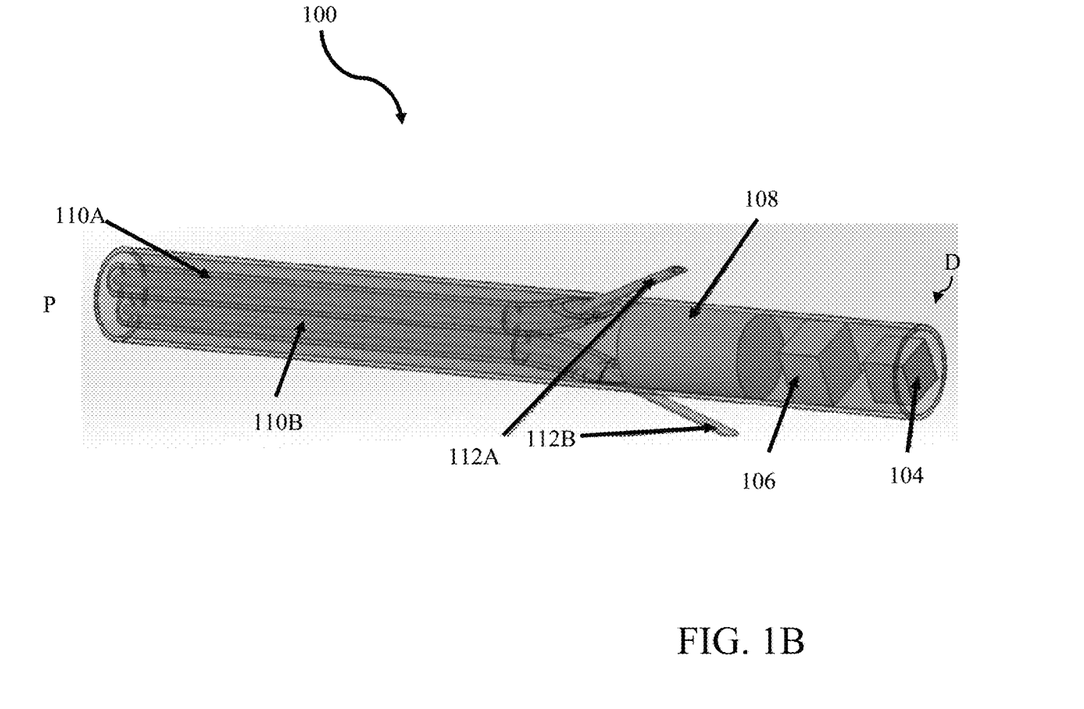

FIGS. 1A and 1B are perspective views of a lung biopsy system 100 according to an embodiment. System 100 includes a housing 102, a camera 104, a light-emitting diode (LED) 106, an ultrasonic sensor 108, a first biopsy needle tube 110A having a first biopsy needle aperture 111A, and a second biopsy needle tube 110B having a second biopsy needle aperture 111B. FIG. 1B additionally depicts a first biopsy needle 112A and a second biopsy needle 112B. System 100 is sized for deployment via a bronchoscope to a remote location of a pulmonary system. Bronchoscopes are standardized devices with a diameter of 5.3 mm. Within each bronchoscope are several standard ports, including a tool port having a diameter of about 2 mm. A bronchoscope can be used to enter a pulmonary system but often cannot be extended all the way to an object that a physician wishes to biopsy because the pulmonary passageways are not wide enough for the bronchoscope to pass through. Rather than access the object using a transthoracic needle, system 100 can be deployed from the tool port and, due to its smaller diameter, routed more easily to objects that are positioned along pulmonary passageways having a smaller diameter.

System 100 has a proximal end P, which can be manipulated by the physician at the bronchoscope or outside of the patient. System 100 also has a distal end D, which can be driven through pulmonary passageways.

Housing 102 is an outer wall of system 100, housing the other components of system 100. Housing 102 can be made from a flexible material such as a polymer, in embodiments. In some embodiments, it may be desirable for housing 102 to be at least partially made of a transparent or translucent material, such that light can pass through housing 102. Housing 102 extends from a proximal end (at or near the bronchoscope; not shown) to a distal end D (at or near camera 104).

Camera 104 is arranged at or near the distal end D of housing 102. Camera 104 can be used to provide an indication of the position of system 100 in a pulmonary system. Camera 104 can send back signals to the physician that show what is in front of system 100, either wirelessly or through a wired connection (not shown) extending from the proximal end to the distal end D of system 100. Camera 104 can provide feedback on the actual position of system 100 in the pulmonary passage. This solves a problem of conventional systems, in that navigational feedback from EBUS or ENB systems can be incorrect and make advancement difficult.

Figure 1C:
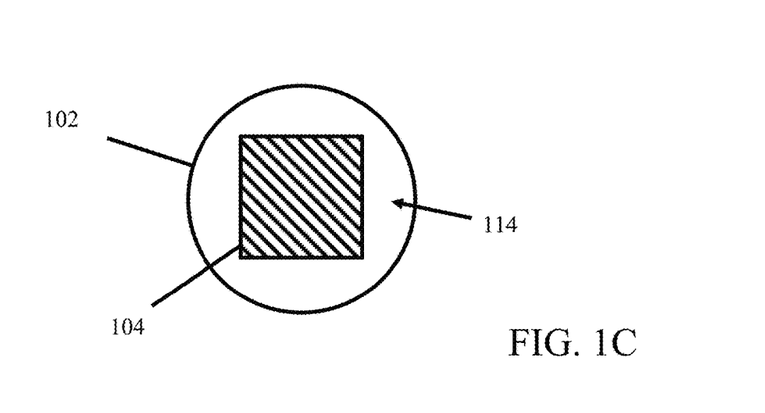
FIG. 1C is a side view of the lung biopsy tool of FIGS. 1A and 1B, from the distal end.

Camera 104 can be, for example, a 1 mm×1 mm square camera. In other embodiments, the size and shape of camera 104 can vary. For example, in alternative embodiments camera 104 could have a round profile from distal end D, Camera 104 is small enough, however, that when positioned in housing 102 having a circular outer diameter, at least some portion of the distal end D of housing 102 is not overlapped by camera 104, as shown in FIG. 1C.

LED 106 is positioned closer to the proximate end than camera 104 of system 100. LED 106 can have a larger cross-sectional area than camera 104 when viewed from the distal end D. In this way, light from LED 106 passes around camera 104 and out the distal end D of system 100, lighting the pulmonary passageways so that camera 104 can be used to provide information about the position of system 100. The light from LED 106 can pass through the distal end D of system 100 due to the fact that the material making up housing 102 is transparent or translucent, in embodiments. In alternative embodiments, LED 106 need not have a larger cross-sectional area than camera 104. For example, in some embodiments outer housing 102 can be made of a transparent or translucent matter, as described above. In those embodiments, light can be routed, either through reflections or refractions, around camera 104. Light can therefore be directed to the distal end D of system 100. In alternative embodiments, LED 106 could be replaced by some other source of illumination. In embodiments, the illumination provided by LED 106 or another light source could be at an angle and wavelength that promotes total internal reflection within the material that makes up outer housing 102 or another transmissive material arranged between camera 104 and outer housing 102. In embodiments, LED 106 or another source of illumination is tuned to the wavelengths or color spectra corresponding to those that are easily detected by camera 104. Additionally or alternatively, LED 106 or another source of illumination can be tuned to a wavelength that is primarily reflected from pulmonary passages rather than absorbed.

In some embodiments, outer housing 102 can be a molded or extruded polymer that encapsulates both camera 104 and LED 106, and outer housing 102 can act as a carrier for the light produced by LED 106. In other embodiments, alternative systems for delivering light to the distal end D of system 100 could be used. For example, fiber optics or other light guides could be used to route light from LED 106 to the distal end D of system 100.

Ultrasonic sensor 108 is arranged along system 100 coaxially with camera 104 and LED 106. This coaxial arrangement allows outer housing 102 to be substantially narrower than if the same components were arranged in another fashion. Ultrasonic sensor 108 can emit and/or detect ultrasonic signal passing through adjacent objects, such as the pulmonary passageway. Tumors, nodules, or other objects that a physician may wish to biopsy often have different acoustical properties in the ultrasonic frequencies than the rest of a pulmonary passageway. Using the signal detected by ultrasonic sensor 108, a physician can determine that ultrasonic sensor 108 is adjacent to the object of interest for biopsy.

First biopsy needle tube 110A and second biopsy needle tube 110B extend within the region bounded by outer housing 102, from the proximal end of system 100 to first and second apertures 111A and 111B that are arranged almost as far in the distal direction as ultrasonic sensor 108. As shown in FIG. 1B, first and second biopsy needles 112A and 112B can be deployed such that a biopsy sample is acquired from a region adjacent to ultrasonic sensor 108.

First and second biopsy needles 112A and 112B can be bendable and can comprise a flexible material such as a polymer, in embodiments. In some embodiments, it may be desirable for first and second biopsy needles 112A and 112B to comprise polyether ether ketone (PEEK) such that the material is high strength, biocompatible, and able to hold a sharpened edge. In other embodiments, it may be desirable for first and second biopsy needles 112A and 112B to comprise a steel cutting tip and a polymer shaft. In still other embodiments, first and second biopsy needles 112A and 112B can comprise Nitinol such that the needles 112A and 112B are able to sustain greater bend angles without kinking when compared to, e.g., steel needles because of the relative yield strengths of these materials. In further embodiments, first and second biopsy needles 112A and 112B can comprise combinations of these materials and/or other materials that provide desired properties and behaviors.

FIG. 1C is an end view of system 100 of FIGS. 1A and 1B, from the distal end D. As shown in FIG. 1C, camera 104 covers some but not all of the distal end D. The rest of the distal end D, circumscribed by outer housing 102 and not covered by the face of camera 104, is a light transmission region 114. It is through this region 114 that light from LED 106 can pass, to illuminate the area in front of camera 104. In embodiments, optical light guides (not shown) can be used to guide the light around the periphery of camera 104.

Figure 1D:
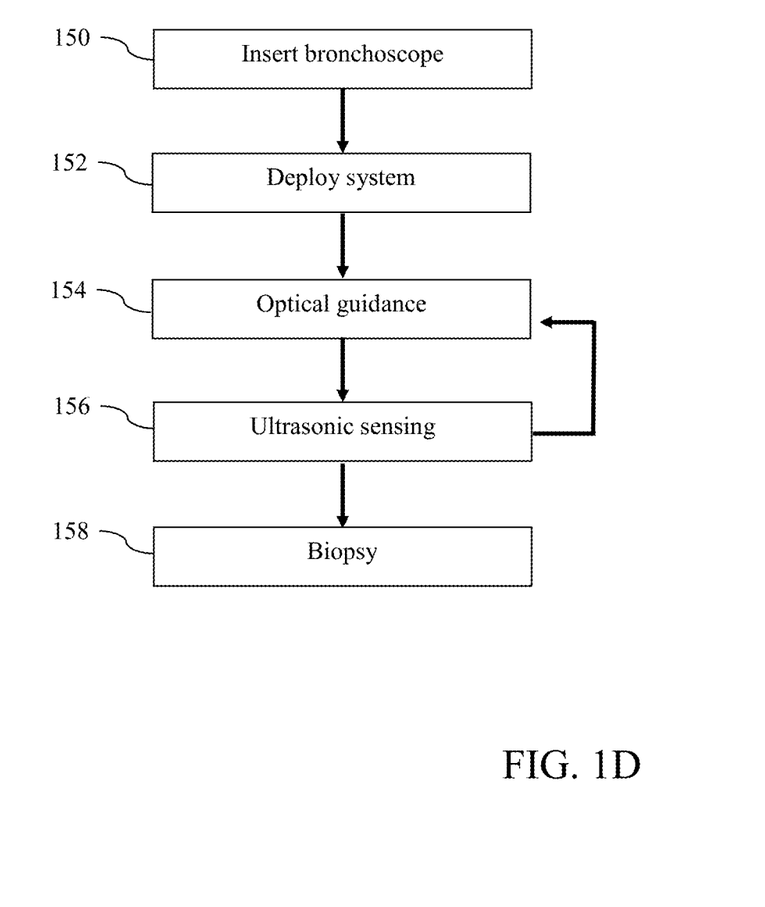
FIG. 1D is a flowchart of a method for operating the system of FIGS. 1A-1C

The components described so far can be used to position system 100 adjacent to an object in a narrow passage of a pulmonary system. FIG. 1D depicts a method for using system 100, according to an embodiment.

According to the method depicted in FIG. 1D, a bronchoscope is inserted into a pulmonary system (150). The bronchoscope includes a tool port, and the system 100 can be deployed therefrom (152). System 100 can be deployed when, for example, the bronchoscope is too large to access a region where an object is located in a pulmonary system. In an alternative, system 100 can be deployed independently, without a bronchoscope. In such an embodiment, the process begins with deployment (152) rather than bronchoscope insertion (150). Once deployed, system 100 can be routed to that object by an operator, using optical guidance (154) provided by the system 100 and its associated camera 104. While system 100 is driven, using optical guidance from camera 104, ultrasonic sensing (156) is employed via ultrasonic sensor 108. Once ultrasonic sensing 156 shows that the object is adjacent to ultrasonic sensor 108, system 100 can be used to biopsy the object (158). System 100 can then be retracted into the bronchoscope and the bronchoscope can be removed from the pulmonary system.

Figure 2A:
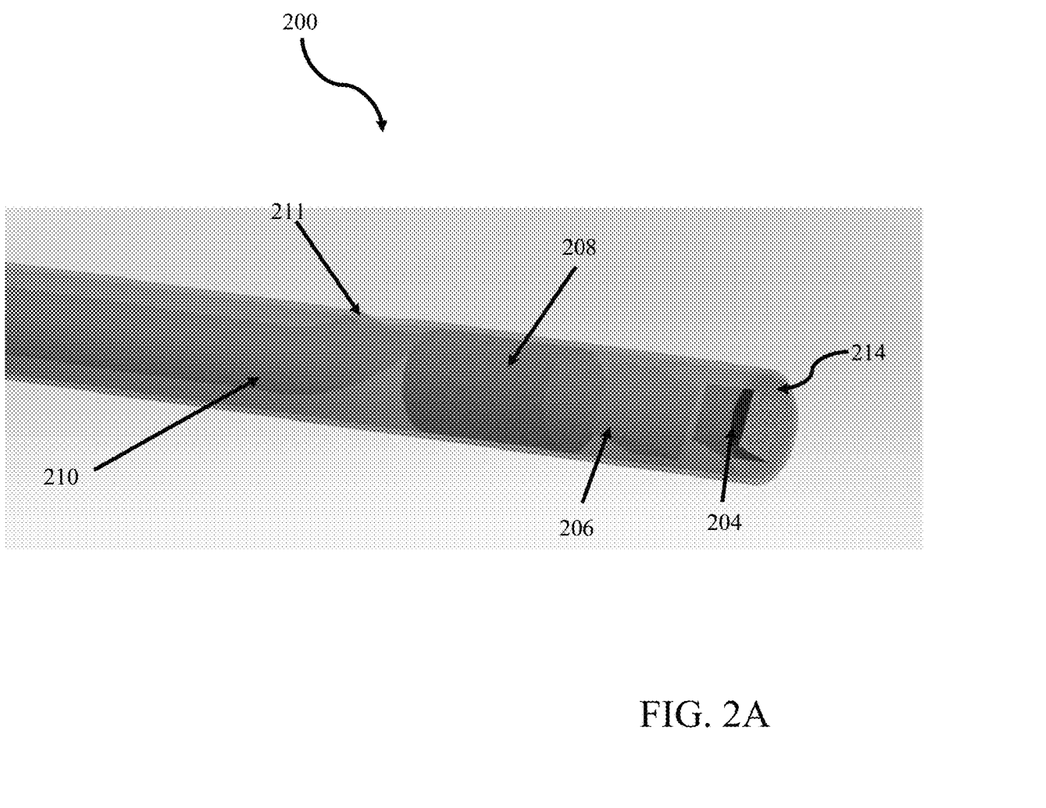
FIGS. 2A and 2B are perspective views of a single-needle lung biopsy tool according to an embodiment.
Figure 2B:
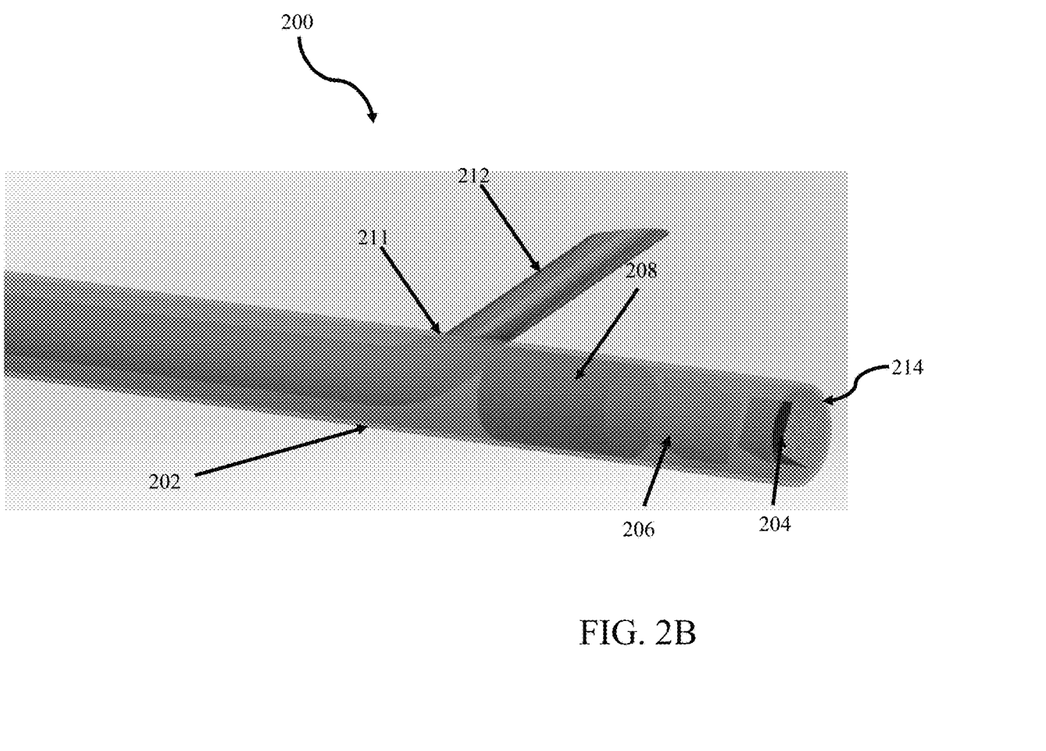

FIGS. 2A-2B depict an alternative embodiment, in which only a single biopsy needle is present. As shown in FIGS. 2A-2B, similar components to those previously described with respect to FIGS. 1A-1C are given similar reference numerals, iterated by a factor of 100. This convention for identifying similar components is used throughout this application with respect to all of the figures.

Like the system 100 of FIGS. 1A-1C, system 200 of FIGS. 2A-2B includes coaxially aligned structures including a camera 204, an LED 206, an ultrasonic sensor 208, a biopsy needle tube 210 terminating at an aperture 211, and a biopsy needle 212 that can be selectively deployed or retracted. Like the system 100 of FIGS. 1A-1C, system 200 of FIGS. 2A-2B can be used to provide optical data and feedback so that an operator at the proximal end can guide it safely through relatively small pulmonary passages that could not be accessed by a bronchoscope. Finally, like the system 100 of FIGS. 1A-1C, system 200 can biopsy a region adjacent to ultrasonic sensor 208, which is configured to detect a change in acoustical properties indicative of a nodule, tumor, or other object.

Because system 200 only includes one biopsy needle 212, an operator can manipulate system 200 from the proximal end to rotate it into a desired orientation before deploying biopsy needle 212. By making system 200 rotatable and including only a single biopsy needle 212, space requirements of system 200 are even less than the requirements of system 100 previously described with respect to FIGS. 1A-1B. In embodiments, this permits for still further reduction in diameter of housing 202, as compared to system 100.

Figure 3A:
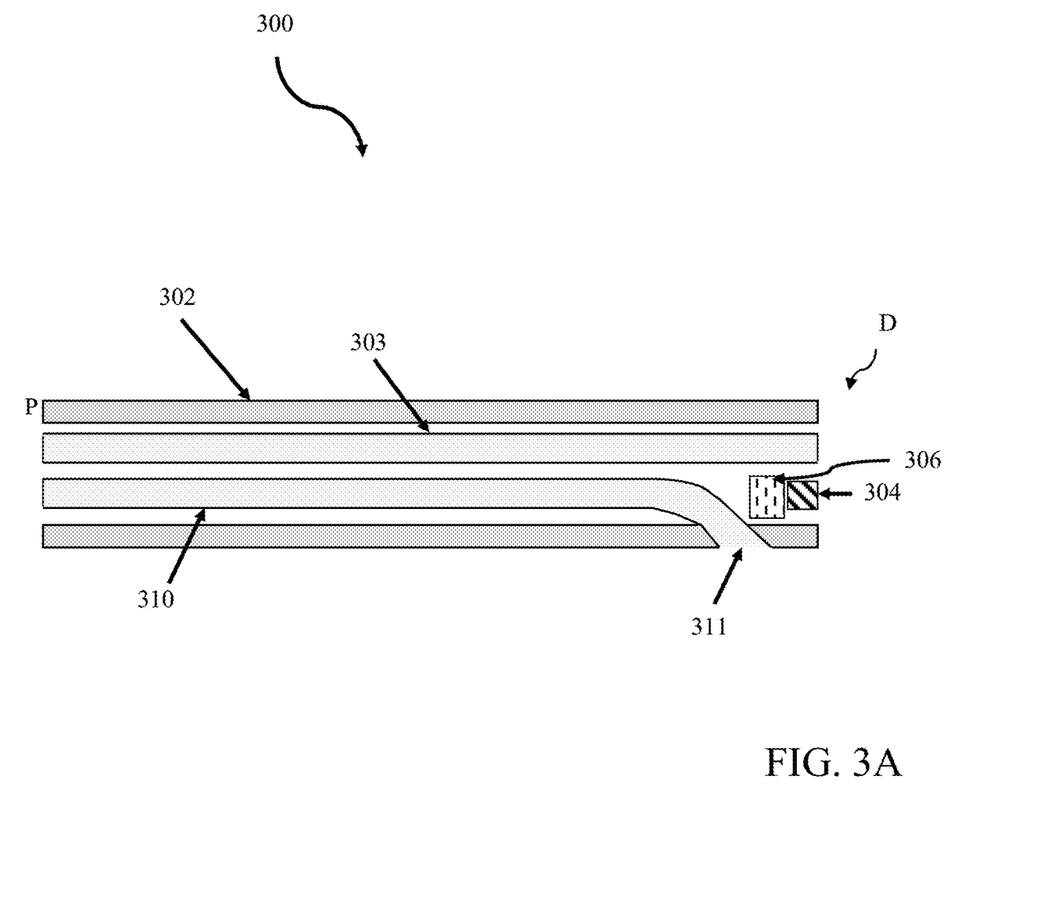
FIGS. 3A and 3B are schematic views of a single-needle lung biopsy tool with a separate tube for an ultrasonic sensor according to an embodiment.
Figure 3B:
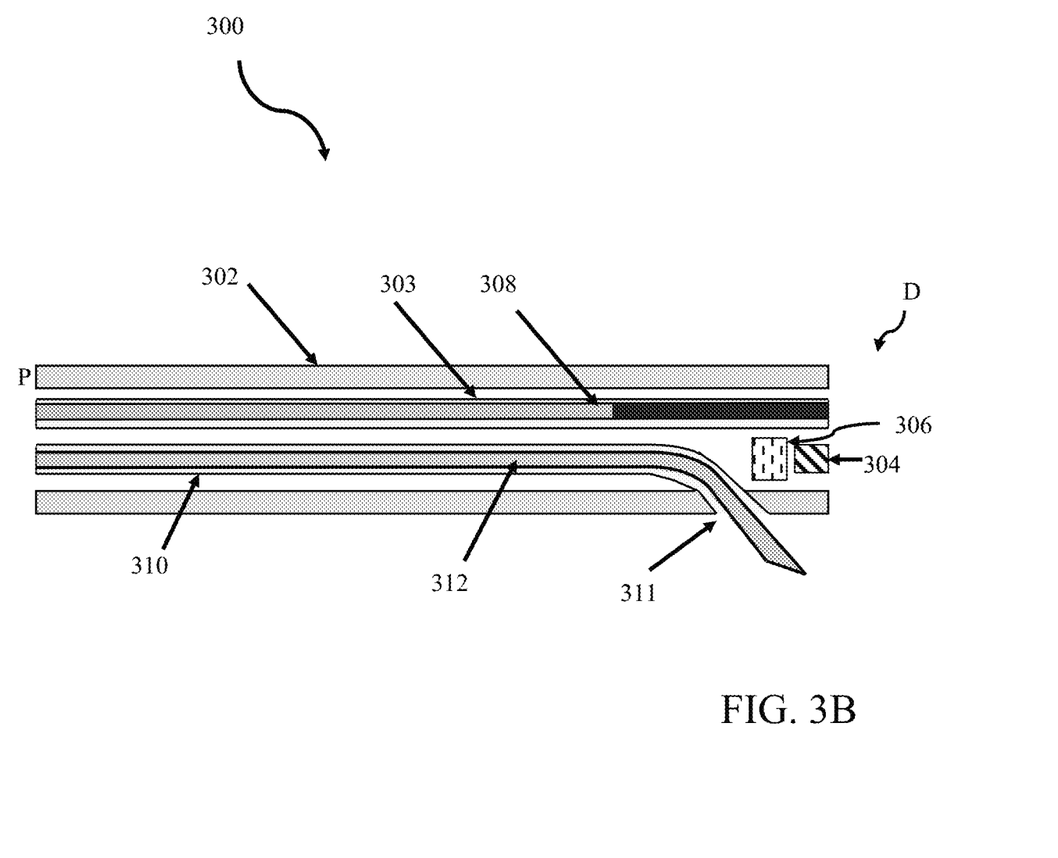

FIGS. 3A-3B depict an alternative embodiment configured to accommodate a single biopsy needle and comprising a second tube 303 to facilitate deployment of an ultrasonic sensor. Like system 100 of FIGS. 1A-1C, system 300 of FIGS. 3A-3B includes a coaxially aligned camera 304, LED 306, and a biopsy needle tube 310 terminating at an aperture 311, and a biopsy needle 312 that can be selectively deployed or retracted. Tube 303 is arranged adjacent to camera 304 and LED 306 and extends within the region bounded by housing 302, from the proximal end P of housing 302 to the distal end D. An ultrasonic sensor 308 can be deployed via tube 303. Ultrasonic sensor 308 can be any EBUS probe that fits within tube 303 and is configured to detect a change in acoustical properties indicative of a nodule, tumor, or other object.

Like the system 100 of FIGS. 1A-1C, system 300 of FIGS. 3A-3B can be used to provide optical data and feedback so that an operator at the proximal end can guide system 300 safely through relatively small pulmonary passages that could not be accessed by a bronchoscope. Using the signal detected by ultrasonic sensor 308, a physician can determine that ultrasonic sensor 308 is adjacent to an object of interest for biopsy.

Figure 4A:
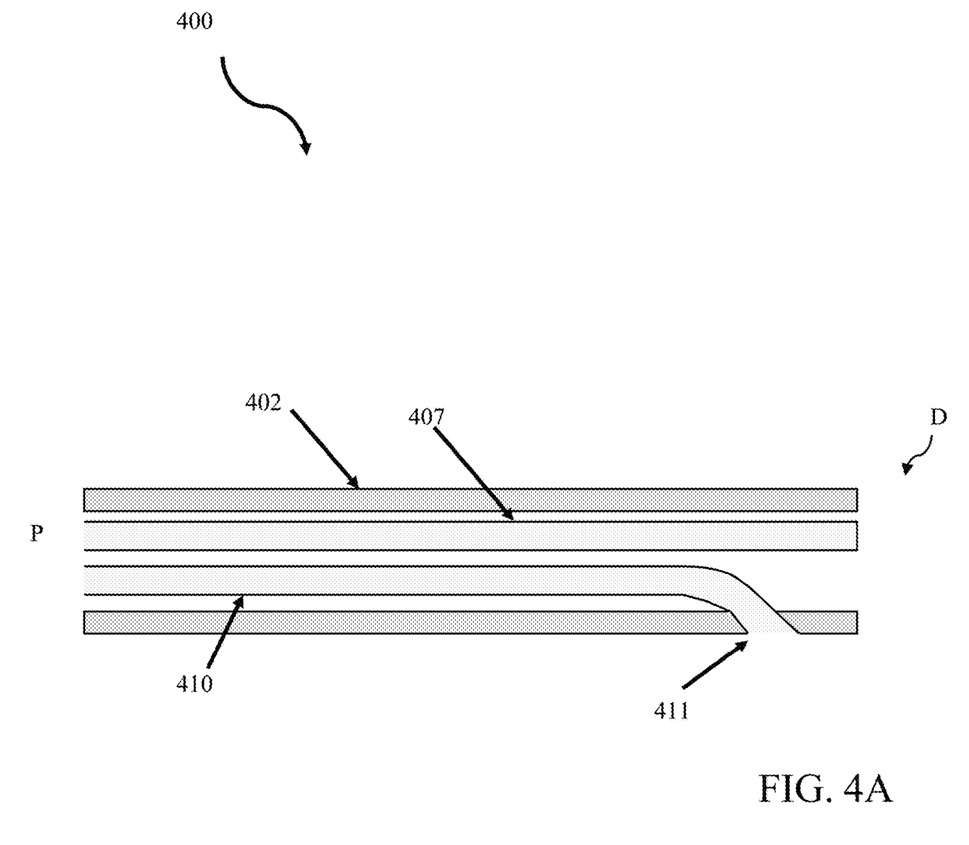
FIGS. 4A-4C are schematic views of a single-needle lung biopsy tool with a separate tube that allows an ultrasonic sensor to be interchanged with a camera and LED module, according to an embodiment.
Figure 4B:
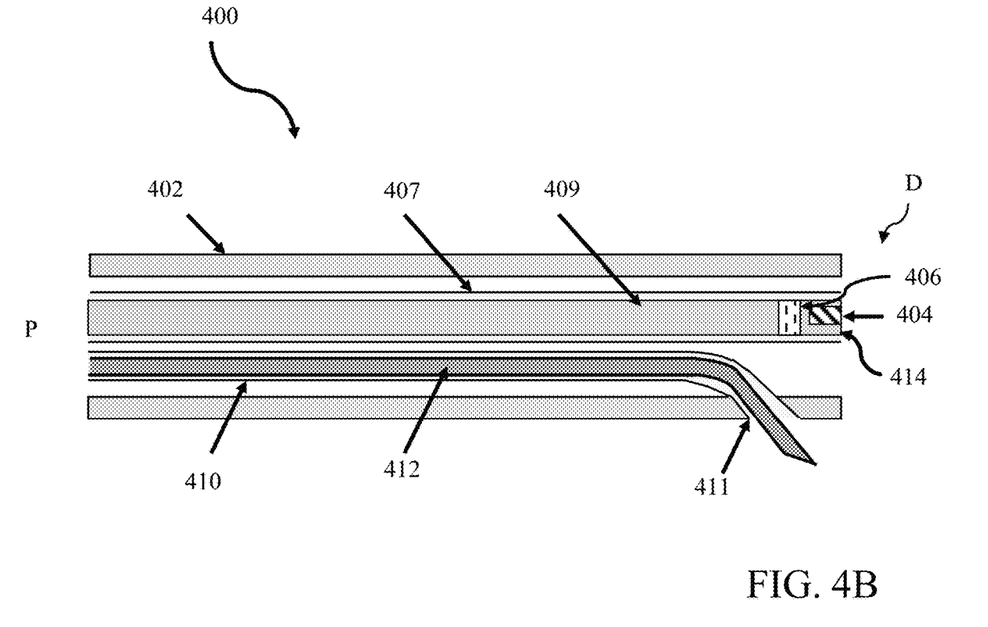
Figure 4C:
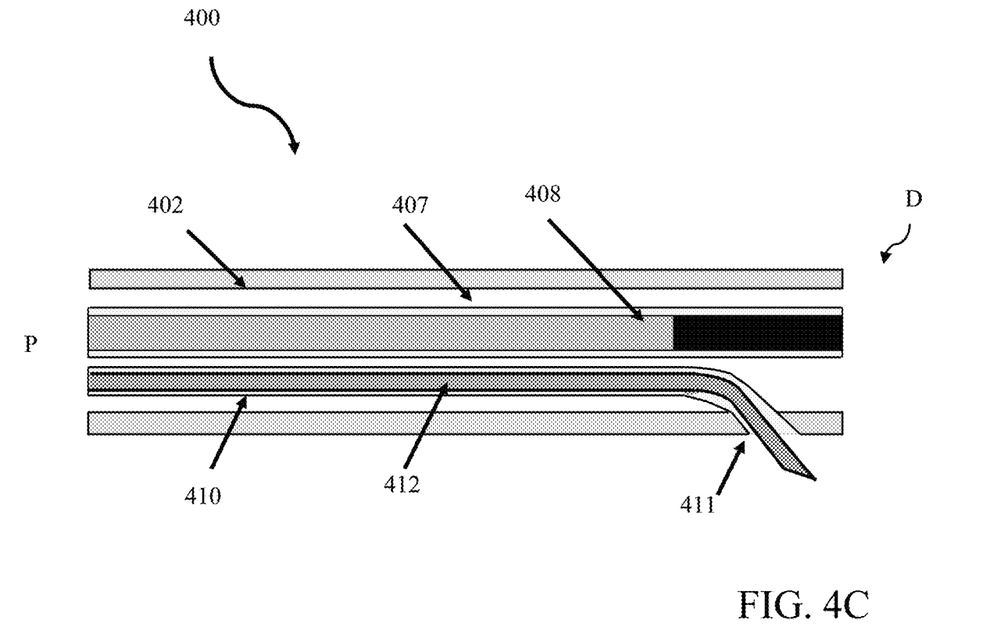

FIGS. 4A-4C depict another embodiment, in which a camera and LED module 409 is interchangeable with an ultrasonic sensor. Like the system 100 of FIGS. 1A-1B, system 400 of FIGS. 4A-4C includes a biopsy needle tube 410 terminating at an aperture 411 in housing 402 before the distal end D of housing 402. A biopsy needle 412 can be selectively deployed or retracted via tube 410. Tube 407 is arranged adjacent to biopsy needle tube 410 within housing 402, from the proximal end P of housing 402 to the distal end D. Like the system 300 of FIGS. 3A-3B, an ultrasonic sensor 408 can be deployed via tube 407 (see FIG. 4C). A module 409 containing a coaxially aligned camera 404 and LED 406 can be interchanged with ultrasonic sensor 408 for deployment via tube 407 (see FIG. 4B).

Like the system 100 of FIGS. 1A-1B, system 400 of FIGS. 4A-4C can be used to provide optical data and feedback so that an operator at the proximal end can guide system 400 safely through relatively small pulmonary passages that could not be accessed by a bronchoscope. The operator can utilize module 409 to navigate to a region of interest. The operator can then interchange ultrasonic sensor 408 with module 409 in order to biopsy a region adjacent to ultrasonic sensor 408.

Figure 5:
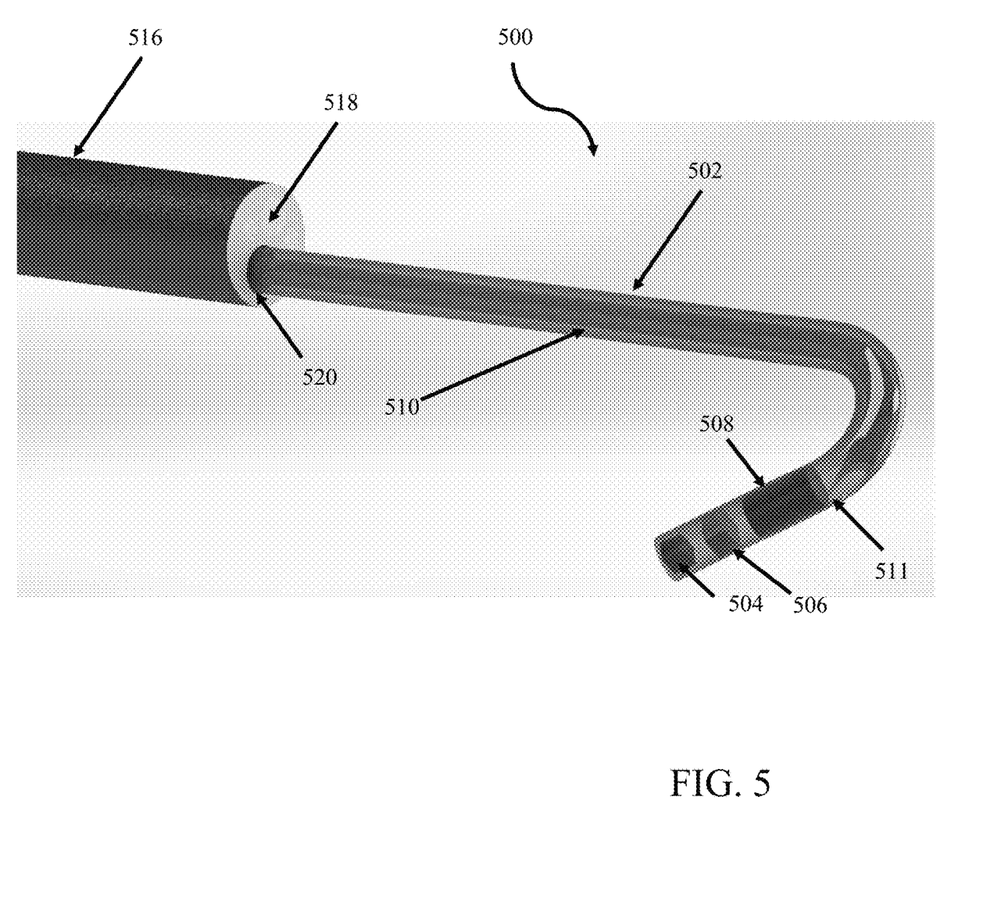
FIG. 5 is a perspective view of a deformable lung biopsy tool positioned in a bronchoscope according to an embodiment.

FIG. 5 is a perspective view of a system 500, in which coaxially aligned camera 504, LED 506, and ultrasonic system 508 are arranged within a housing 502. System 500 extends from a bronchoscope 516. Bronchoscope 516 includes a distal end 518 having several ports. Tool port 520 is about 2 mm or less in diameter on standard bronchoscopes. When bronchoscope 516 reaches a portion of a pulmonary system where it can go no further due to its size, system 500 can be deployed to go further and potentially reach an object of interest for biopsy.

As shown in FIG. 5, system 500 can also selectively curve. Housing 502 can be made of a deformable material in embodiments, such as a polymer. Depending on the location of the curve and the extent of the curvature, there may be some misalignment of camera 504, LED 506, and ultrasonic system 508 from perfect coaxial alignment. Perfect alignment is not necessary, however, so long as light from LED 506 can pass around camera 504 either through housing 502 or another optically transmissive region (e.g., 114, 214). Curvature may be desirable where the passageway in the pulmonary system to the object of interest is curved. An operator can cause deformation of the housing 502 to follow the passageway without causing discomfort or injury to the patient by curving the housing 502 appropriately, in embodiments. The amount of curvature can be determined by the operator by using data from camera 504.

Figures 6A, 6B:
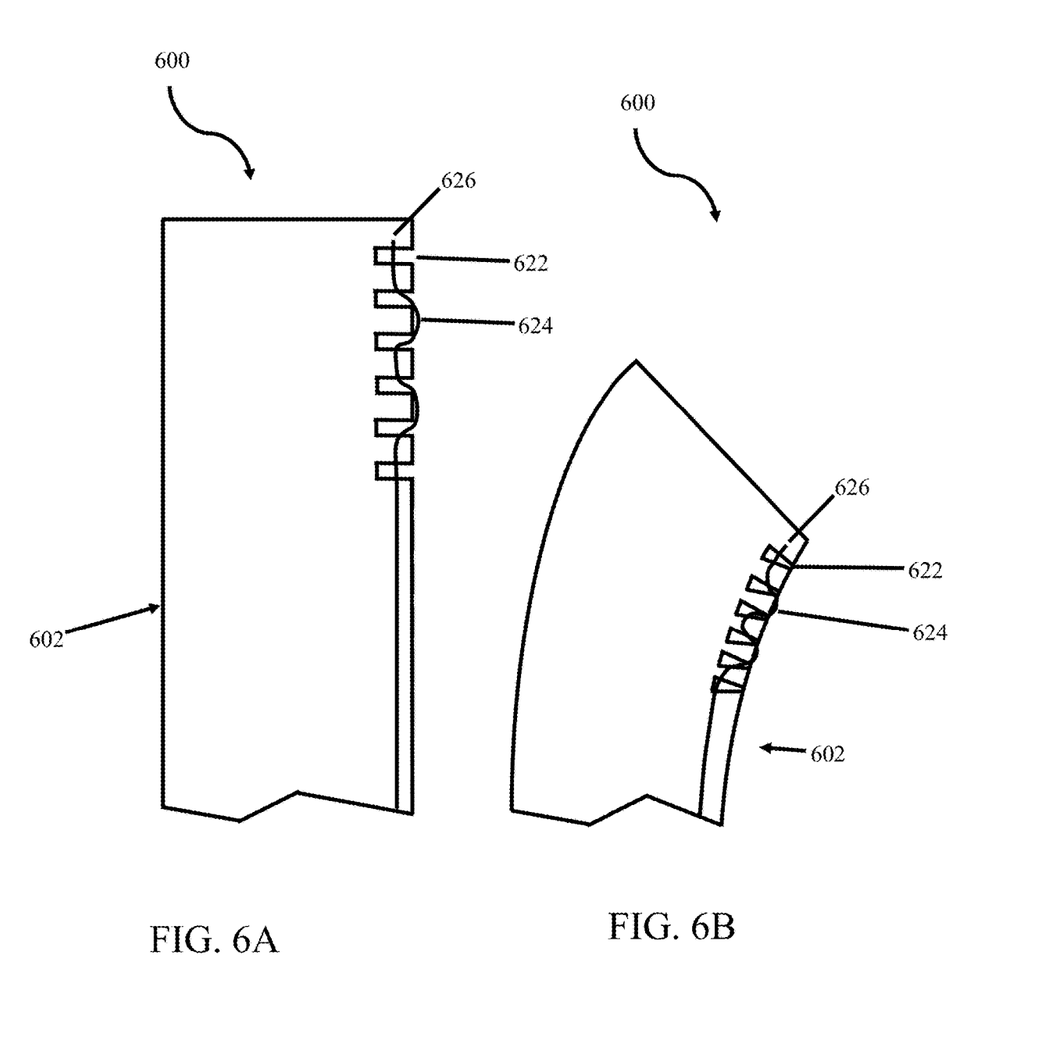
FIGS. 6A-6D are schematic views depicting a system for deforming a lung biopsy tool according to an embodiment.

FIGS. 6A-6D depict a mechanism for selectively causing curvature of a system as previously shown with respect to FIG. 5. An un-deflected view is shown in FIG. 6A. Housing 602 of a system 600 includes a plurality of apertures 622, threaded by cable 624. Cable 624 is anchored at anchor point 626. In order to cause curvature of housing 602, an operator can pull or otherwise manipulate the cable 624.

As shown in FIG. 6B, with the cable pulled, housing 602 bends, and apertures 622 are deformed to permit for more easy compression of the side of deflection. In embodiments, apertures 622 can be arranged on multiple sides of housing 602 (e.g., on two sides, spaced 180 degrees apart from each other around the outer circumference of housing 602), so that deflection in more than one direction is possible. Alternatively, in embodiments in which system 600 can be rotated, the operator can rotate housing 602 such that apertures 622 are arranged on the side to which the operator would like to turn. In such embodiments, a single set of apertures 622 arranged along one side of housing 602 can be sufficient to turn system 600 as needed.

Figure 6C:
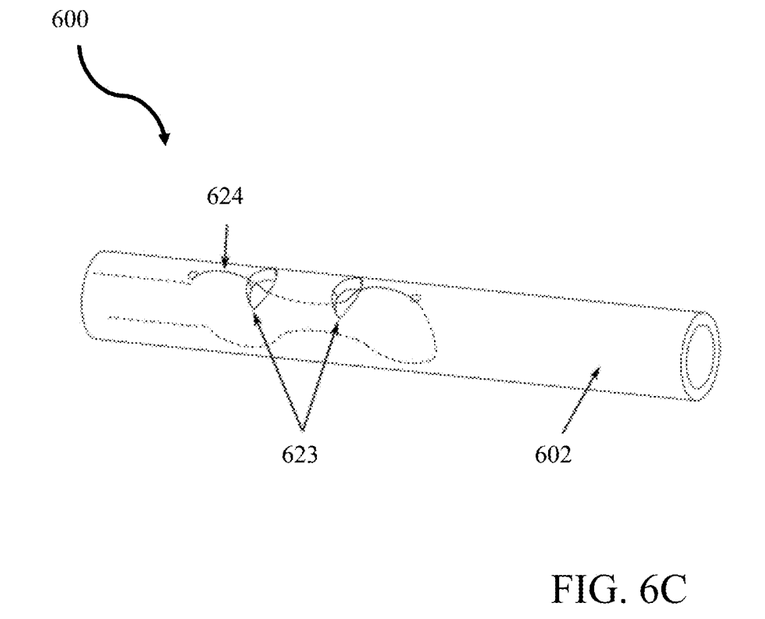
Figure 6D:
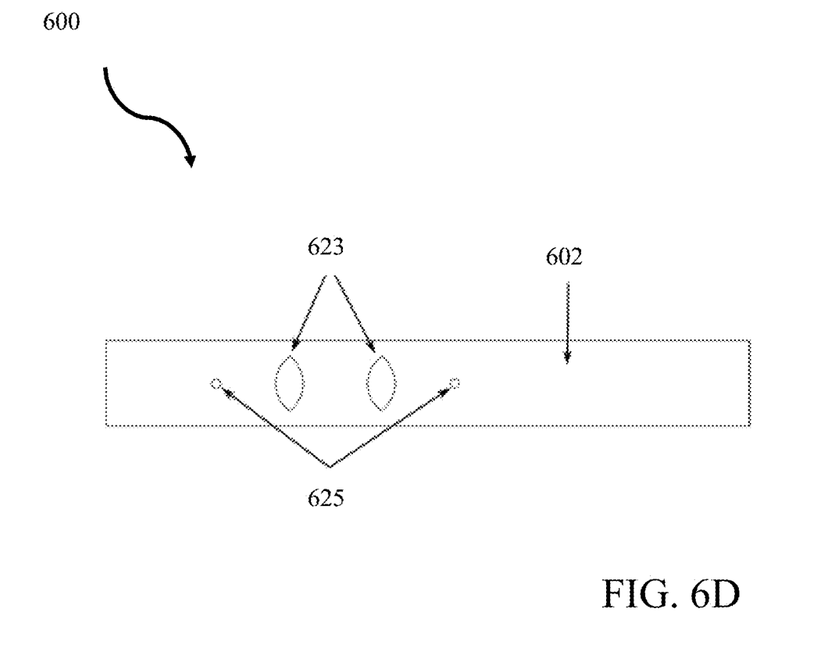

FIGS. 6C and 6D depict an example geometry of apertures 622 for the threading of cable 624, in which the plurality of apertures 622 comprises at least two notches 623 and at least two holes 625. Notches 623 are arranged intermediate holes 625 and have a lens shape to facilitate bending of the tube. Other shapes or configurations of notches 623 can be implemented in other embodiments. Holes 625 are small, in one embodiment having a diameter that is slightly larger than cable 624. Holes 625 constrain the direction of bending and prevent twisting of housing 602 when it is being angulated. More or fewer apertures 622, of the configuration of notches 625 or holes 623, can be included in other embodiments, and the particular configuration, relative arrangement and spacings of the apertures 622 can vary from the examples depicted according to a particular application or use of system 600. Additionally, apertures 622 of system 600 can be incorporated in other embodiments discussed herein.

In alternative embodiments, other systems could be used, rather than a cable 624 attached at an anchor point 626, to turn system 600. For example, housing 602 could include a memory-shape component such as a Nitinol wire, or a piezoelectric actuator, or some other remotely-operated system for turning the distal end of system 600. System 600 could also be steerable using either one or two angulation wires, similar to how traditional bronchoscopes are angulated, in alternative embodiments.

Figure 7:
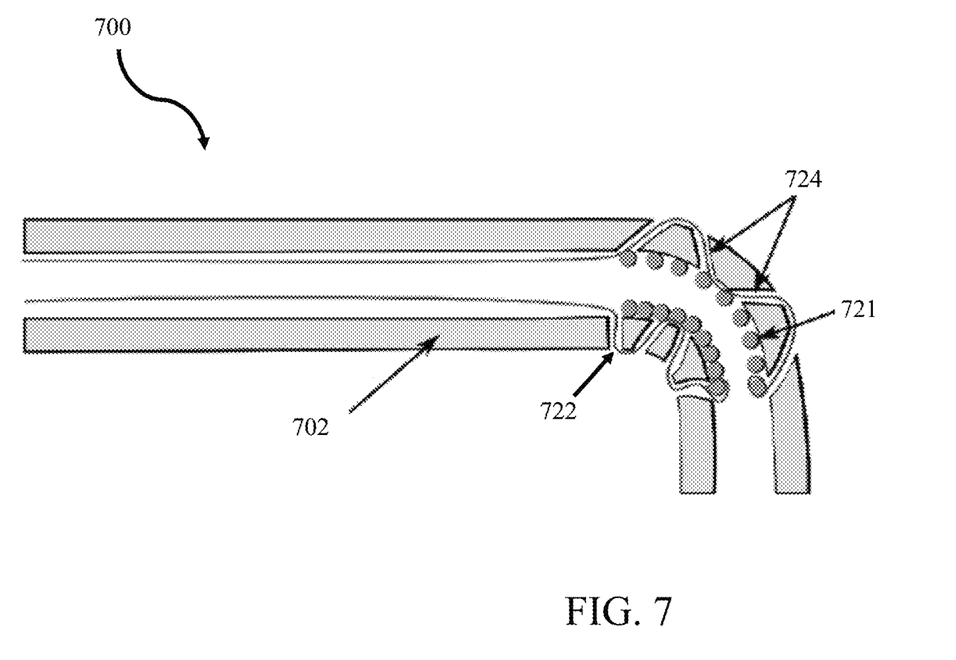
FIG. 7 is a schematic view depicting a coil spring system for preventing kinking and facilitating straightening of a lung biopsy tool according to an embodiment.

FIG. 7 depicts system 700, which additionally comprises at least one coil spring 721 to facilitate straightening and prevent kinking of housing 702 as it is selectively curved or otherwise directed. Coil spring 721 is arranged in the interior of housing 702 of system 700 and can have an outer diameter that is slightly smaller than an inner diameter of housing 702. Like housing 602 of system 600, housing 702 includes several notches 722 threaded by cable 724. Cable 724 is anchored at the distal end of coil spring system 721. Like in system 600, in order to cause curvature of housing 702, an operator can pull or otherwise manipulate cable 724. Coil spring system 721 prevents kinking of housing 702 while the housing is curved by providing internal support. Coil spring system 721 then facilitates straightening of housing 702 when the operator manipulates the cable to straighten system 700.

In alternative embodiments, similar systems could be employed in other contexts. For example, rather than being used in a pulmonary system, a similar device could be sized to fit through other passages such as vasculature. In those embodiments, the relative size of the outer housing could be different in order to accommodate the expected size of the passages through which that system will pass, and the port, device, or catheter from which the system will be deployed. Likewise, the size and materials making up the camera, and the intensity or wavelength of the light source, can be varied to match the application.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

By integrating camera and illumination in a single device having a small enough diameter to be deployed from the standard tool port of a bronchoscope, access to objects that would normally require expensive ENB is provided. In addition, the potential hazards associated with transthoracic needle puncture are reduced. This system is affordable enough to be used at medical centers that do not currently have ENB systems.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A lung biopsy system comprising:
a housing extending from a proximal end to a distal end;
a first tube configured to enable deployment of a biopsy needle and extending from the proximal end of the housing to a first aperture in the housing before the distal end;
an ultrasonic system configured to be arranged in the housing at the distal end;
a camera configured to be arranged in the housing proximate the distal end to obtain optical data relating to a position of the system; and
a light source configured to be arranged in the housing proximate the camera to produce illumination for the camera,
wherein the camera, the light source, the ultrasonic system, and the biopsy needle tube are arranged in order coaxially in the housing from the distal end to the proximal end.

2. The lung biopsy system of claim 1, wherein the housing is made of a transparent material.

3. The lung biopsy system of claim 1, further comprising a light guide to route light from the light source to the distal end.

4. The lung biopsy system of claim 1, further comprising a second tube arranged within the housing opposite the first tube to enable deployment of a biopsy needle and extending from the proximal end to a second aperture in the housing before the distal end.

5. The lung biopsy system of claim 1, wherein the housing further comprises a plurality of lens-shaped notches formed in an exterior surface of the housing, and wherein the system further comprises a cable configured to be threaded through the lens-shaped notches.

6. The lung biopsy system of claim 5, wherein the system further comprises a coil spring arranged in the housing adjacent the cable.

7. The lung biopsy system of claim 1, wherein the first tube is configured to accommodate a biopsy needle comprising a flexible shaft and a steel tip.

* * * * *